United States Patent
Minagawa

(10) Patent No.: US 9,758,605 B2
(45) Date of Patent: Sep. 12, 2017

(54) SURFACE MODIFICATION METHOD AND SURFACE-MODIFIED ELASTIC BODY

(71) Applicant: SUMITOMO RUBBER INDUSTRIES, LTD., Kobe-shi, Hyogo (JP)

(72) Inventor: Yasuhisa Minagawa, Kobe (JP)

(73) Assignee: SUMITOMO RUBBER INDUSTRIES, LTD., Kobe-Shi, Hyogo (JP)

(*) Notice: Subject to any disclaimer, the term of this patent is extended or adjusted under 35 U.S.C. 154(b) by 0 days.

(21) Appl. No.: 14/437,584

(22) PCT Filed: Nov. 19, 2013

(86) PCT No.: PCT/JP2013/081090
§ 371 (c)(1),
(2) Date: Apr. 22, 2015

(87) PCT Pub. No.: WO2014/080873
PCT Pub. Date: May 30, 2014

(65) Prior Publication Data
US 2015/0284487 A1    Oct. 8, 2015

(30) Foreign Application Priority Data
Nov. 20, 2012  (JP) ................ 2012-254328

(51) Int. Cl.
*C08F 136/18*    (2006.01)
*C08J 7/18*    (2006.01)
(Continued)

(52) U.S. Cl.
CPC .......... *C08F 136/18* (2013.01); *A61M 5/28* (2013.01); *A61M 5/31513* (2013.01); *B60C 1/00* (2013.01);
(Continued)

(58) Field of Classification Search
CPC ........ C08F 7/18; C08F 136/02; C08F 136/14; C08F 136/16; A61M 5/3153; A61M 5/28;
(Continued)

(56) References Cited

U.S. PATENT DOCUMENTS 3,418,066 A    12/1968    Caldwell et al.
5,100,689 A    3/1992    Goldberg et al.
(Continued)

FOREIGN PATENT DOCUMENTS

CN    101565489 A    10/2009
CN    102382291 A    3/2012
(Continued)

OTHER PUBLICATIONS

International Search Report, issued in PCT/JP2013/081090, dated Jan. 21, 2014.
(Continued)

*Primary Examiner* — Sanza McClendon
(74) *Attorney, Agent, or Firm* — Birch, Stewart, Kolasch & Birch, LLP

(57) ABSTRACT

The present invention provides methods for surface-modifying a rubber vulcanizate or a thermoplastic elastomer, which can cost-effectively provide a variety of functions, such as sliding properties, according to the application. The present invention relates to a method for surface-modifying a rubber vulcanizate or a thermoplastic elastomer as a target for modification, the method including: step 1 of forming polymerization initiation points on a surface of the modification target; and step 2 of radically polymerizing a non-functional monomer, starting from the polymerization initiation points, to grow non-functional polymer chains, and then radically polymerizing a fluoropolyether segment-containing functional monomer to grow functional polymer chains.

21 Claims, 2 Drawing Sheets

(51) Int. Cl.

| | | |
|---|---|---|
| *B60C 1/00* | (2006.01) | |
| *A61M 5/31* | (2006.01) | |
| *A61M 5/28* | (2006.01) | |
| *A61M 5/315* | (2006.01) | |
| *C08L 101/00* | (2006.01) | |
| *B60C 11/13* | (2006.01) | |
| *C08F 136/16* | (2006.01) | |

(52) U.S. Cl.
CPC ........ *B60C 1/0016* (2013.01); *B60C 11/1346* (2013.01); *C08F 136/16* (2013.01); *C08J 7/18* (2013.01); *C08L 101/00* (2013.01); *C08J 2300/26* (2013.01); *C08J 2321/00* (2013.01)

(58) Field of Classification Search
CPC ................ C08J 2321/00; C08J 2323/26; C08J 2323/28; C08J 2300/26; C08J 2300/22
See application file for complete search history.

(56) References Cited

U.S. PATENT DOCUMENTS

| | | | |
|---|---|---|---|
| 5,154,727 A | 10/1992 | Dyer | |
| 5,340,879 A | 8/1994 | Audenaert et al. | |
| 5,453,467 A | 9/1995 | Bamford et al. | |
| 5,637,460 A | 6/1997 | Swan et al. | |
| 5,688,252 A | 11/1997 | Matsuda et al. | |
| 5,855,623 A | 1/1999 | English et al. | |
| 5,885,566 A | 3/1999 | Goldberg | |
| 5,889,073 A | 3/1999 | Zhang et al. | |
| 5,967,714 A | 10/1999 | Ottersbach et al. | |
| 6,001,894 A | 12/1999 | Ottersbach et al. | |
| 6,188,075 B1 | 2/2001 | Takayama et al. | |
| 6,203,856 B1 | 3/2001 | Ottersbach et al. | |
| 6,228,172 B1 | 5/2001 | Taylor et al. | |
| 6,358,557 B1 | 3/2002 | Wang et al. | |
| 6,808,738 B2 | 10/2004 | DiTizio et al. | |
| 7,348,055 B2 | 3/2008 | Chappa et al. | |
| 8,299,139 B1 | 10/2012 | Taranekar et al. | |
| 8,840,927 B2 | 9/2014 | Ditizio et al. | |
| 9,339,845 B2 | 5/2016 | Minagawa | |
| 9,469,736 B2 | 10/2016 | Minagawa | |
| 2002/0161065 A1 | 10/2002 | DiTizio et al. | |
| 2004/0086568 A1 | 5/2004 | DiTizio et al. | |
| 2004/0106732 A1 | 6/2004 | Tsuji et al. | |
| 2005/0137355 A1 | 6/2005 | Buckanin et al. | |
| 2006/0155057 A1 | 7/2006 | Hermeling et al. | |
| 2007/0003592 A1 | 1/2007 | Hissink | |
| 2007/0116971 A1 | 5/2007 | Yoshikawa et al. | |
| 2008/0016644 A1 | 1/2008 | Mizote et al. | |
| 2008/0103287 A1 | 5/2008 | Chino et al. | |
| 2008/0312377 A1 | 12/2008 | Schmidt et al. | |
| 2009/0169715 A1 | 7/2009 | Dias et al. | |
| 2009/0239089 A1 | 9/2009 | Agata et al. | |
| 2010/0255336 A1 | 10/2010 | Zabinski | |
| 2011/0160357 A1 | 6/2011 | Gerster et al. | |
| 2011/0274940 A1 | 11/2011 | Kyomoto et al. | |
| 2012/0021151 A1 | 1/2012 | Tatarka et al. | |
| 2012/0100369 A1 | 4/2012 | Hanazawa et al. | |
| 2013/0203883 A1 | 8/2013 | Minagawa | |
| 2013/0274367 A1 | 10/2013 | Minagawa et al. | |
| 2013/0310772 A1 | 11/2013 | Minagawa | |
| 2014/0039084 A1 | 2/2014 | Minagawa | |
| 2014/0128493 A1 | 5/2014 | Minagawa | |
| 2015/0203612 A1 | 7/2015 | Minagawa | |

FOREIGN PATENT DOCUMENTS

| | | |
|---|---|---|
| EP | 0 872 512 A2 | 10/1998 |
| EP | 2 623 335 A2 | 8/2013 |
| EP | 2 664 627 A1 | 11/2013 |
| EP | 2 796 155 A1 | 10/2014 |
| EP | 2 894 191 A1 | 7/2015 |
| GB | 1120803 A | 7/1968 |
| GB | 1120804 A | 7/1968 |
| JP | 61-209667 A | 9/1986 |
| JP | 62-87163 A | 4/1987 |
| JP | 63-92658 A | 4/1988 |
| JP | 5-43634 A | 2/1993 |
| JP | 5-179055 A | 7/1993 |
| JP | 6-25450 A | 2/1994 |
| JP | 6-510322 A | 11/1994 |
| JP | 7-100744 B2 | 11/1995 |
| JP | 8-1793 A | 1/1996 |
| JP | 9-31361 A | 2/1997 |
| JP | 9-67457 A | 3/1997 |
| JP | 9-108359 A | 4/1997 |
| JP | 9-313594 A | 12/1997 |
| JP | 10-90500 A | 4/1998 |
| JP | 10-251350 A | 9/1998 |
| JP | 10-298320 A | 11/1998 |
| JP | 11-192305 A | 7/1999 |
| JP | 2000-273229 A | 10/2000 |
| JP | 2001-31871 A | 2/2001 |
| JP | 2001-46956 A | 2/2001 |
| JP | 2001-95621 A | 4/2001 |
| JP | 2002-145971 A | 5/2002 |
| JP | 2002-544346 A | 12/2002 |
| JP | 2003-2903 A | 1/2003 |
| JP | 2003-510378 A | 3/2003 |
| JP | 2004-528418 A | 9/2004 |
| JP | 2004-298220 A | 10/2004 |
| JP | 2005-516736 A | 6/2005 |
| JP | 2005-213516 A | 8/2005 |
| JP | 2005-523981 A | 8/2005 |
| JP | 2005-253538 A | 9/2005 |
| JP | 2007-77286 A | 3/2007 |
| JP | 2007-119563 A | 5/2007 |
| JP | 2007-145884 A | 6/2007 |
| JP | 2007-514861 A | 6/2007 |
| JP | 2009-30074 A | 2/2009 |
| JP | 2009-518479 A | 5/2009 |
| JP | 2009-138169 A | 6/2009 |
| JP | 2009-226718 A | 10/2009 |
| JP | 2009-227842 A | 10/2009 |
| JP | 2010-23710 A | 2/2010 |
| JP | 2010-142537 A | 7/2010 |
| JP | 2010-142573 A | 7/2010 |
| JP | 2010-150349 A | 7/2010 |
| JP | 4523532 B2 | 8/2010 |
| JP | 2010-216964 A | 9/2010 |
| JP | 2011-42755 A | 3/2011 |
| JP | 2011-67362 A | 4/2011 |
| JP | 2011-188908 A | 9/2011 |
| JP | 2011-189562 A | 9/2011 |
| JP | 2011-208133 A | 10/2011 |
| JP | 2011-219520 A | 11/2011 |
| JP | 2011-241190 A | 12/2011 |
| JP | 2012-105579 A | 6/2012 |
| JP | 2012-162646 A | 8/2012 |
| JP | 2013-159629 A | 8/2013 |
| JP | 2013-208777 A | 10/2013 |
| JP | 2013-237801 A | 11/2013 |
| JP | 2013-237802 A | 11/2013 |
| WO | WO 93/05081 A1 | 3/1993 |
| WO | WO 03/068289 A1 | 8/2003 |
| WO | WO 03/093357 A1 | 11/2003 |
| WO | WO 2007/065721 A2 | 6/2007 |
| WO | WO 2007/072613 A1 | 6/2007 |
| WO | WO 2010/058848 A1 | 5/2010 |
| WO | WO 2010/131652 A1 | 11/2010 |
| WO | WO 2011/038483 A1 | 4/2011 |
| WO | WO 2012/091169 A1 | 7/2012 |
| WO | WO 2012/165525 A1 | 12/2012 |

OTHER PUBLICATIONS

Allmér et al., "Surface Modification of Polymers, I. Vapour Phase Photografting with Acrylic Acid," Journal of Polymer Science: Part A: Polymer Chemistry, vol. 26, 1988, pp. 2099-2111.

International Search Report, dated Dec. 3, 2013, for International Application No. PCT/JP2013/074219.

(56) References Cited

OTHER PUBLICATIONS

International Search Report, dated Jul. 24, 2012, for International Application No. PCT/JP2012/064030.
U.S. Non-Final Office Action, dated May 8, 2015, for U.S. Appl. No. 13/756,837.
U.S. Non-Final Office Action, dated Oct. 20, 2014, for U.S. Appl. No. 13/756,837.
U.S. Notice of Allowance, dated Dec. 26, 2014, for U.S. Appl. No. 13/956,974.
U.S. Office Action (Requirement for Restriction/Election), dated May 9, 2014, for U.S. Appl. No. 13/956,974.
U.S. Office Action, dated Apr. 17, 2015, for U.S. Appl. No. 13/775,451.
U.S. Office Action, dated Aug. 25, 2014, for U.S. Appl. No. 13/956,974.
U.S. Office Action, dated Jun. 24, 2015, for U.S. Appl. No. 14/118,136.
U.S. Office Action, dated Sep. 21, 2015, for U.S. Appl. No. 14/107,746.
International Search Report and Written Opinion of the International Searching Authority, dated Jan. 20, 2015, for International Application No. PCT/JP2014/079947.
International Search Report, dated Aug. 19, 2014, for International Application No. PCT/JP2014/063268.
International Search Report, dated Feb. 25, 2014, for International Application No. PCT/JP2013/082409.
Jinan Haohua Industry Co., Ltd., "Ethanaminum, N,N,N-trimethyl-2-[(2-methyl-1-oxo-2-propen-1-yl) oxy]-, chloride (1:1)," CAS: 5039-78-1, Product Information Inquiry Description, found online on Dec. 27, 2016, pp. 1-2 (3 pages), http://guide7932.guidechem.com/pro-show2436647.html.
U.S. Office Action, dated Nov. 3, 2016, for U.S. Appl. No. 14/896,096.
Machine English translation JP 2011-241190 A published Dec. 1, 2011.
Machine English translation of JP 2012-162646 A published Aug. 30, 2012.
Machine English translation of JP 6-25450 A published Feb. 1, 1994.
Machine English translation of JP 9-31361 A published Feb. 4, 1997.

SURFACE MODIFICATION METHOD AND SURFACE-MODIFIED ELASTIC BODY

TECHNICAL FIELD

The present invention relates to surface modification methods and surface-modified elastic bodies, such as a gasket for syringes at least part of whose surface is modified by the modification method, and a tire at least part of whose groove surface is modified by the modification method.

BACKGROUND ART

In view of the importance of sealing properties, elastic bodies such as rubber are used in parts which slide while maintaining their sealing performance, for example a gasket which is integrated with a syringe plunger and forms a seal between the plunger and barrel. Unfortunately, such elastic bodies have a slight problem with the sliding properties (see Patent Literature 1). Thus, a sliding property improving agent, for example silicone oil, is applied to the sliding surface. However, a concern has been raised over the potential adverse effects of silicone oil on recently marketed bio-preparations. On the other hand, gaskets not coated with a sliding property improving agent have poor sliding properties and thus do not allow plungers to be smoothly pushed but cause them to pulsate during administration, leading to problems such as an inaccurate injection amount and infliction of pain on patients.

To satisfy the conflicting requirements, sealing properties and sliding properties, a coating technique using a self-lubricating PTFE film has been proposed (see Patent Literature 2). Unfortunately, such PTFE films are generally expensive and increase the production cost of processed products. Thus, the range of applications of these films is limited. Also, products coated with PTFE films might not be reliable when they are used in applications where sliding or the like is repeated and thus durability is required. Furthermore, since PTFE is vulnerable to radiation, the PTFE-coated products unfortunately cannot be sterilized by radiation.

Consideration may also be given to the use in other applications where sliding properties are required in the presence of water. Specifically, water can be delivered without a loss by reducing the fluid resistance of the inner surface of a pre-filled syringe or of the inner surface of a pipe or tube for delivering water, or by increasing or markedly reducing the contact angle with water. Drainage of water on wet roads and of snow on snowy roads can be improved by reducing the fluid resistance of the groove surfaces of tires, or by increasing or markedly reducing the contact angle with water. This results in enhanced grip performance and improved hydroplaning performance and therefore better safety. In addition, less adhesion of dirt and dusts can be expected when the sliding resistance of the sidewall surfaces of tires or the walls of buildings is reduced, or when their contact angle with water is increased.

Further advantageous effects can be expected, including, for example: less pressure loss upon delivering water, an aqueous solution or the like through a diaphragm such as a diaphragm pump or valve; easy sliding of skis and snowboards achieved by enhancing the sliding properties of the sliding surfaces thereof; better noticeability of road signs and signboards achieved by enhancing the sliding properties thereof to allow snow to readily slide on the surface; reduction in water resistance or drag on the outer peripheries of ships and less adhesion of bacteria on the outer peripheries, achieved by reducing the sliding resistance of the outer peripheries or by increasing the contact angle with water; and reduction in water resistance or drag of swimsuits achieved by improving the sliding properties of the thread surfaces thereof.

CITATION LIST

Patent Literature

Patent Literature 1: JP 2004-298220 A
Patent Literature 2: JP 2010-142573 A

SUMMARY OF INVENTION

Technical Problem

The present invention aims to solve the above problems and provide methods for surface-modifying a rubber vulcanizate or a thermoplastic elastomer, which can cost-effectively provide a variety of functions, such as sliding properties, according to the application. The present invention also aims to provide surface-modified elastic bodies, such as a gasket for syringes at least part of whose surface is modified by the surface modification method, and a tire at least part of whose groove surface is modified by the method.

Solution to Problem

The present invention relates to a method for surface-modifying a rubber vulcanizate or a thermoplastic elastomer as a target for modification, the method including: step 1 of forming polymerization initiation points on a surface of the modification target; and step 2 of radically polymerizing a non-functional monomer, starting from the polymerization initiation points, to grow non-functional polymer chains, and then radically polymerizing a fluoropolyether segment-containing functional monomer to grow functional polymer chains.

The step 1 preferably includes adsorbing a photopolymerization initiator onto a surface of the modification target, optionally followed by irradiation with LED light having a wavelength of 300 to 400 nm, to form polymerization initiation points from the photopolymerization initiator on the surface.

The step 2 preferably includes radically polymerizing a non-functional monomer, starting from the polymerization initiation points, by irradiation with LED light having a wavelength of 300 to 450 nm to grow non-functional polymer chains, and then radically polymerizing a fluoropolyether segment-containing functional monomer by irradiation with LED light having a wavelength of 300 to 450 nm to grow functional polymer chains.

The rubber vulcanizate or thermoplastic elastomer preferably contains an allylic carbon atom which is adjacent to a double bond.

The photopolymerization initiator is preferably at least one of a benzophenone compound and a thioxanthone compound.

In the step 2, a reducing agent or an antioxidant is preferably added in the radical polymerization of the non-functional monomer and/or of the fluoropolyether segment-containing functional monomer. The reducing agent or antioxidant is preferably at least one selected from the group consisting of riboflavin, ascorbic acid, α-tocopherol, β-carotene, and uric acid.

The surface modification method preferably includes inserting an inert gas into a reaction container and a reaction solution during or before the light irradiation, and polymerizing the monomer in an atmosphere replaced with the inert gas.

The non-functional monomer is preferably at least one selected from the group consisting of acrylic acid, acrylic acid esters, acrylamide, dimethylacrylamide, diethylacrylamide, isopropylacrylamide, hydroxyacrylamide, acryloylmorpholine, acrylic acid alkali metal salts, acrylic acid amine salts, methacrylic acid, methacrylic acid esters, methacrylamide, methacrylic acid alkali metal salts, methacrylic acid amine salts, and acrylonitrile.

Preferably, the fluoropolyether segment in the fluoropolyether segment-containing functional monomer is a perfluoropolyether segment having at least one of the following units (A) to (D):
(A): —$(CF_2O)_a$—,
(B): —$(CF_2CF_2O)_b$—,
(C): —$(CF_2CF_2CF_2O)_c$—, and
(D): —$(CF(CF_3)CF_2O)_d$—
wherein a, b, c, and d each represent 0 or a positive integer and satisfy the relation: $2 \leq a+b+c+d \leq 200$.

Preferably, the fluoropolyether segment-containing functional monomer is a monomer represented by the following formula:

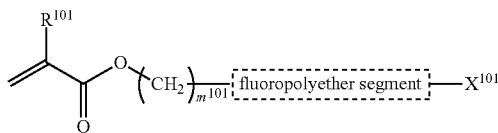

wherein $R^{101}$ represents a methyl group, an ethyl group, a hydrogen atom, a fluorine atom, a chlorine atom, or a bromine atom; $m^{191}$ represents an integer of 0 to 5; $X^{101}$ represents a hydrogen atom or a fluorine atom; and the fluoropolyether segment is a perfluoropolyether segment having at least one of the following units (A) to (D):
(A): —$(CF_2O)_a$—,
(B): —$(CF_2CF_2O)_b$—,
(C): —$(CF_2CF_2CF_2O)_c$—, and
(D): —$(CF(CF_3)CF_2O)_d$—
wherein a, b, c, and d each represent 0 or a positive integer and satisfy the relation: $2 \leq a+b+c+d \leq 200$.

Preferably, the fluoropolyether segment-containing functional monomer is a monomer represented by the following formula:

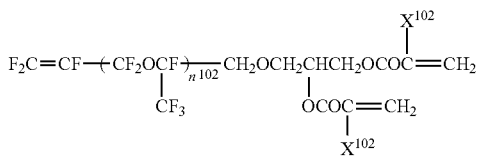

wherein $n^{102}$ represents an integer of 0 to 100; and $X^{102}$ represents H or F.

In the surface modification method, preferably the (liquid) non-functional monomer, the (liquid) fluoropolyether segment-containing functional monomer, or a solution thereof contains a polymerization inhibitor, and is polymerized in the presence of the polymerization inhibitor. The polymerization inhibitor is preferably 4-methylphenol.

Preferably, a length of the entire polymer chain, including the non-functional polymer chain and the functional polymer chain, is 10 to 50000 nm.

Preferably, a ratio in length of the non-functional polymer chain to the functional polymer chain is 50:50 to 99.9:0.1.

The present invention relates to a surface-modified elastic body, which is obtained by the surface modification method.

The present invention relates to a surface-modified elastic body, which is obtained by the surface modification method, the elastic body being required to have sliding properties, low friction, or low water resistance in the presence of water or in a dry state.

The present invention relates to a surface-modified elastic body, including a three-dimensional solid at least part of whose surface is modified by the surface modification method.

The surface-modified elastic body preferably includes a polymer brush.

The present invention relates to a gasket for syringes, at least part of whose surface is modified by the surface modification method.

The present invention also relates to a tire, at least part of whose groove surface is modified by the surface modification method.

Advantageous Effects of Invention

The present invention provides a method for surface-modifying a rubber vulcanizate or a thermoplastic elastomer as a target for modification, the method including: step 1 of forming polymerization initiation points on a surface of the modification target; and step 2 of radically polymerizing a non-functional monomer, starting from the polymerization initiation points, to grow non-functional polymer chains, and then radically polymerizing a fluoropolyether segment-containing functional monomer to grow functional polymer chains. Such a method can cost-effectively provide a variety of functions, such as excellent sliding properties, to the surface of the modification target and, at the same time, can also provide good sealing properties. Thus, by forming polymer chains on the surface of targets by the method, surface-modified elastic bodies, such as a gasket for syringes, can be provided which are excellent in the above properties.

DESCRIPTION OF EMBODIMENTS

Figure 1:
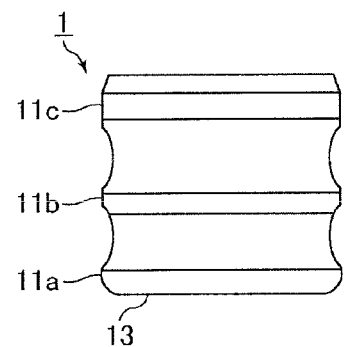
FIG. 1 is an exemplary side view of an embodiment of a gasket for syringes.

The present invention relates to a method for surface-modifying a rubber vulcanizate or a thermoplastic elastomer as a target for modification, the method including: step 1 of forming polymerization initiation points on a surface of the modification target; and step 2 of radically polymerizing a non-functional monomer, starting from the polymerization initiation points, to grow non-functional polymer chains, and then radically polymerizing a fluoropolyether segment-containing functional monomer to grow functional polymer chains (fluoropolyether segment-containing functional polymer chains).

To provide a desired function by forming polymer chains on the surface of a rubber vulcanizate or thermoplastic elastomer which usually has large irregularities, it is necessary to form polymer chains having a certain height (length) from the surface with functional polymer chains being disposed on the top. Since functional monomers are usually very expensive, the use of these monomers is economically disadvantageous unless the amount of polymer chains formed from these monomers is the minimum amount required to produce the desired function. In contrast, the present invention provides a surface modification method in which polymer chains are first formed from inexpensive non-functional monomers on the surface of a modification target to build a certain scaffold, and then a fluoropolyether segment-containing functional monomer is polymerized to build up a minimum amount of functional polymer chains on the scaffold, whereby a functional polymer layer is formed on the outermost surface. Thus, the present invention can very cost-effectively provide surface-modified elastic bodies that are imparted with desired functions, such as sliding properties.

Moreover, since the fluoropolyether segment-containing functional monomer used in the present invention has low surface free energy, forming functional polymer chains from the monomer on the outermost surface provides a surface having high sliding properties.

The step 1 includes forming polymerization initiation points on a surface of a vulcanized rubber or a molded thermoplastic elastomer (modification target).

The rubber vulcanizate or thermoplastic elastomer may suitably contain a carbon atom adjacent to a double bond (i.e., allylic carbon atom).

Examples of rubber that may be used as the modification target include diene rubbers such as styrene-butadiene rubber, polybutadiene rubber, polyisoprene rubber, natural rubber, and deproteinized natural rubber; and butyl rubber and halogenated butyl rubber which have a degree of unsaturation of a few percent of isoprene units. The butyl rubber or halogenated butyl rubber, if used, is preferably a rubber cross-linked by triazine because the amount of matter extracted from the rubber vulcanizate is small. In this case, the rubber may contain an acid acceptor. Examples of suitable acid acceptors include hydrotalcite and magnesium carbonate.

If other rubbers are used, preferably sulfur vulcanization is performed. In such cases, compounding ingredients commonly used for sulfur vulcanization may be added, such as vulcanization accelerators, zinc oxide, filler, and silane coupling agents. Suitable examples of the filler include carbon black, silica, clay, talc, and calcium carbonate.

The vulcanization conditions for the rubber may be appropriately set. The rubber is preferably vulcanized at 150° C. or higher, more preferably 170° C. or higher, still more preferably 175° C. or higher.

Examples of the thermoplastic elastomer include polymer compounds that have rubber elasticity at room temperature owing to aggregates of plastic components (hard segments) serving as crosslinking points (e.g., thermoplastic elastomers (TPE) such as styrene-butadiene-styrene copolymer); and polymer compounds having rubber elasticity, obtained by mixing a thermoplastic component and a rubber component and dynamically crosslinking the mixture by a crosslinking agent (e.g., thermoplastic elastomers (TPV) such as polymer alloys containing a styrenic block copolymer or olefinic resin and a cross-linked rubber component).

Other examples of suitable thermoplastic elastomers include nylon, polyester, polyurethane, polypropylene, and dynamically cross-linked thermoplastic elastomers thereof. Preferred among dynamically cross-linked thermoplastic elastomers are those obtained by dynamically crosslinking halogenated butyl rubber in a thermoplastic elastomer. This thermoplastic elastomer is preferably nylon, polyurethane, polypropylene, styrene-isobutylene-styrene block copolymer (SIBS), or the like.

The polymerization initiation points may be formed, for example, by adsorbing a photopolymerization initiator onto a surface of the modification target. Examples of the photopolymerization initiator include carbonyl compounds, organic sulfur compounds such as tetraethylthiuram disulfide, persulfides, redox compounds, azo compounds, diazo compounds, halogen compounds, and photoreductive pigments. Carbonyl compounds are especially preferred.

The carbonyl compound as the photopolymerization initiator is preferably benzophenone or its derivative, and may suitably be a benzophenone compound represented by the following formula:

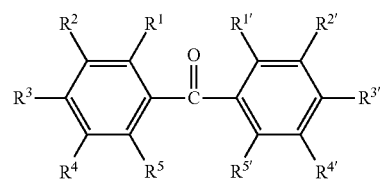

wherein $R^1$ to $R^5$ and $R^{1'}$ to $R^{5'}$ are the same as or different from one another and each represent a hydrogen atom, an alkyl group, a halogen (fluorine, chlorine, bromine, or iodine), a hydroxy group, a primary to tertiary amino group, a mercapto group, or a hydrocarbon group optionally containing an oxygen atom, a nitrogen atom, or a sulfur atom; and any two adjacent groups thereof may be joined to each other to form a cyclic structure together with the carbon atoms to which they are attached.

Specific examples of the benzophenone compound include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Benzophenone, xanthone, and 9-fluorenone are particularly preferred because then good polymer brushes can be formed. Other examples of suitable benzophenone compounds include fluorobenzophenone compounds, such as 2,3,4,5,6-pentafluorobenzophenone and decafluorobenzophenone.

Thioxanthone compounds can also be suitably used as the polymerization initiator because they provide a high polymerization rate and also can easily be adsorbed on and/or reacted with rubber or the like. For example, compounds represented by the following formula can be suitably used.

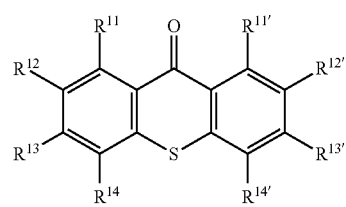

In the formula, $R^{11}$ to $R^{14}$ and $R^{11'}$ to $R^{14'}$ are the same as or different from one another and each represent a hydrogen atom, a halogen atom, an alkyl group, a cyclic alkyl group, an aryl group, an alkenyl group, an alkoxy group, or an aryloxy group.

Examples of thioxanthone compounds represented by the formula include thioxanthone, 2-isopropylthioxanthone, 4-isopropylthioxanthone, 2,3-diethylthioxanthone, 2,4-diethylthioxanthone, 2,4-dichlorothioxanthone, 2-methoxythioxanthone, 1-chloro-4-propoxythioxanthone, 2-cyclohexylthioxanthone, 4-cyclohexylthioxanthone, 2-vinylthioxanthone, 2,4-divinylthioxanthone, 2,4-diphenylthioxanthone, 2-butenyl-4-phenylthioxanthone, 2-methoxythioxanthone, and 2-p-octyloxyphenyl-4-ethylthioxanthone. Preferred among these are the compounds in which one or two, particularly two of the $R^{11}$ to $R^{14}$ and $R^{11'}$ to $R^{14'}$ are substituted with alkyl groups, and more preferred is 2,4-diethylthioxanthone.

The photopolymerization initiator such as benzophenone compound may be adsorbed onto the surface of the modification target by conventionally known methods. In the case of using a benzophenone compound, for example, the benzophenone compound is dissolved in an organic solvent to prepare a solution; a surface portion of the target to be modified is treated with this solution so that the compound is adsorbed on the surface; and if necessary, the organic solvent is evaporated off by drying, whereby polymerization initiation points are formed. The surface may be treated by any method that allows the solution of the benzophenone compound to be brought into contact with the surface of the modification target. Suitable methods include application or spraying of the benzophenone compound solution, and immersion into the solution. If only part of the surface needs to be modified, it is sufficient to adsorb the photopolymerization initiator only onto such part of the surface. In this case, for example, application or spraying of the solution is suitable. Examples of the solvent include methanol, ethanol, acetone, benzene, toluene, methyl ethyl ketone, ethyl acetate, and THF. Acetone is preferred because it does not swell the modification target and it can be rapidly dried and evaporated off.

Moreover, after the surface of the modification target portion is treated with the benzophenone compound solution so that the photopolymerization initiator is adsorbed on the surface, the surface of the modification target is preferably further irradiated with light so that the polymerization initiator is chemically bonded to the surface. For example, the benzophenone compound may be fixed on the surface by irradiation with ultraviolet light having a wavelength of 300 to 450 nm, preferably 300 to 400 nm, more preferably 350 to 400 nm. During the step 1 and the fixing, hydrogen is abstracted from the rubber surface and a carbon atom on the rubber surface is then covalently bonded to the carbon atom in C═O of benzophenone while the abstracted hydrogen is bonded to the oxygen atom in C═O to form C—O—H. Moreover, since this hydrogen abstraction reaction selectively occurs on allylic hydrogen atoms in the modification target, the rubber preferably contains a butadiene or isoprene unit that contains an allylic hydrogen atom.

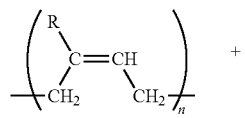

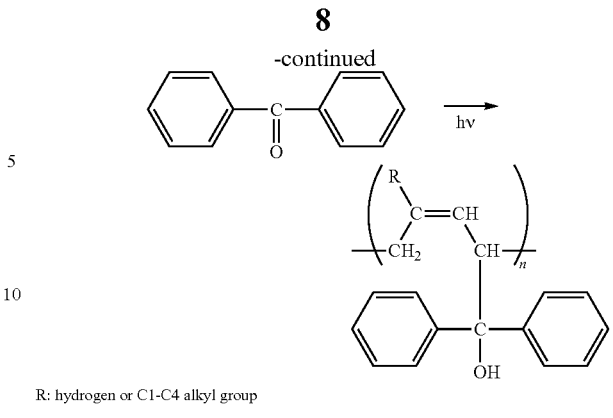

R: hydrogen or C1-C4 alkyl group

In particular, the polymerization initiation points are preferably formed by treating the surface of the modification target with the photopolymerization initiator so that the photopolymerization initiator is adsorbed on the surface, and then irradiating the treated surface with LED light having a wavelength of 300 to 400 nm. Particularly preferably, after the surface of the modification target is treated with the benzophenone compound solution so that the photopolymerization initiator is adsorbed, the treated surface is further irradiated with LED light having a wavelength of 300 to 400 nm so that the adsorbed photopolymerization initiator is chemically bonded to the surface. The LED light suitably has a wavelength of 355 to 380 nm.

The step 2 includes radically polymerizing a non-functional monomer, starting from the polymerization initiation points, to grow non-functional polymer chains, and then radically polymerizing a fluoropolyether segment-containing functional monomer to grow functional polymer chains. Specifically, a non-functional monomer is first radically polymerized, starting from the polymerization initiation points formed in the step 1, to form non-functional polymer chains. Then, a fluoropolyether segment-containing functional monomer is radically polymerized on the resultant non-functional polymer chains to form functional polymer chains while extending the polymer chains. In this manner, a surface-modified elastic body having a functional polymer layer formed on the outermost surface thereof can be prepared.

The non-functional monomer in the step 2 refers to a monomer that forms non-functional polymer chains which do not have functions appropriately chosen according to the application or the like. For example, in cases where sliding properties or other functions are intended to be provided to the modification target, the non-functional monomer is one which does not provide such functions, and may be appropriately selected in view of economic efficiency or the like. The fluoropolyether segment-containing functional monomer, on the other hand, may be one with a fluorine-containing polyether group obtained by replacing a part or all of the hydrogen atoms in a polyether group represented by, for example, —(C(R)$_2$O)$_n$— (e.g., an alkylene oxide group) with a halogen atom, and is capable of providing sliding properties or other properties.

The non-functional monomer may be appropriately selected from the above-mentioned standpoint. Examples include acrylic acid, acrylic acid esters such as methyl acrylate or ethyl acrylate, acrylamide, dimethylacrylamide, diethylacrylamide, isopropylacrylamide, hydroxyacrylamide, acryloylmorpholine, acrylic acid alkali metal salts such as sodium acrylate or potassium acrylate, acrylic acid amine salts, methacrylic acid, methacrylic acid esters such as methyl methacrylate or ethyl methacrylate, methacrylamide, methacrylic acid alkali metal salts such as sodium methacrylate or potassium methacrylate, methacrylic acid amine salts, and acrylonitrile. These may be used alone, or two or more thereof may be used in combination.

The fluoropolyether segment-containing functional monomer is suitably a monomer in which the fluoropolyether segment is a perfluoropolyether segment having at least one of the following units (A) to (D):

(A): $-(CF_2O)_a-$,
(B): $-(CF_2CF_2O)_b-$,
(C): $-(CF_2CF_2CF_2O)_c-$, and
(D): $-(CF(CF_3)CF_2O)_d-$
wherein a, b, c, and d each represent 0 or a positive integer and satisfy the relation: $2 \leq a+b+c+c+d \leq 200$.

The fluoropolyether segment-containing functional monomer is also suitably a monomer represented by the following formula:

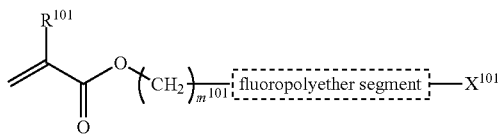

wherein $R^{101}$ represents a methyl group, an ethyl group, a hydrogen atom, a fluorine atom, a chlorine atom, or a bromine atom; $m^{101}$ represents an integer of 0 to 5; $X^{101}$ represents a hydrogen atom or a fluorine atom; and the fluoropolyether segment is a perfluoropolyether segment having at least one of the following units (A) to (D):

(A): $-(CF_2O)_a-$,
(B): $-(CF_2CF_2O)_b-$,
(C): $-(CF_2CF_2CF_2O)_c-$, and
(D): $-(CF(CF_3)CF_2O)_d-$
wherein a, b, c, and d each represent 0 or a positive integer and satisfy the relation: $2 \leq a+b+c+d \leq 200$.

In the perfluoropolyether segment having at least one of the units (A) to (D), the a, b, c, and d are each preferably an integer of 2 to 200, more preferably an integer of 4 to 180, and they preferably satisfy the relation: $4 \leq a+b+c+d \leq 180$.

The fluoropolyether segment-containing functional monomer is also suitably a monomer represented by the following formula:

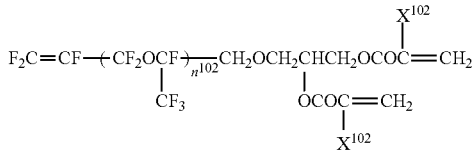

wherein $n^{102}$ represents an integer of 0 to 100; and $X^{102}$ represents H or F.

The $n^{102}$ is preferably an integer of 2 to 80, more preferably an integer of 2 to 20.

In the step 2, the non-functional monomer and the fluoropolyether segment-containing functional monomer may each be radically polymerized as follows. The (liquid) non-functional monomer or fluoropolyether segment-containing functional monomer, or a solution thereof is applied (sprayed) to the surface of the modification target to which a benzophenone compound or the like is adsorbed or covalently bonded, or to the modification target on which non-functional polymer chains are formed. Alternatively, the modification target or the modification target on which non-functional polymer chains are formed is immersed in the (liquid) non-functional monomer or fluoropolyether segment-containing functional monomer, or a solution thereof. Then, the modification target is irradiated with light, such as ultraviolet light, to allow the radical polymerization (photoradical polymerization) of the corresponding monomer to proceed. Thus, non-functional polymer chains and functional polymer chains can be grown in this order on the surface of the modification target. In another method, after the application, the surface may be covered with a transparent sheet of glass, PET, polycarbonate, or the like, followed by irradiating the covered surface with light, such as ultraviolet light, to allow the radical polymerization (photoradical polymerization) of the corresponding monomer to proceed. Thus, non-functional polymer chains and functional polymer chains can be grown in this order on the surface of the modification target.

In the step 2, radical polymerization (photoradical polymerization) is preferably allowed to proceed by irradiating with light the non-functional monomer or fluoropolyether segment-containing functional monomer which contains a reducing agent or an antioxidant added. This is desirable because the reducing agent or antioxidant scavenges oxygen in the system. Regarding the monomer which contains a reducing agent or antioxidant added, these components may be mixed with or separated from each other. Moreover, after the modification target obtained in the step 1 is brought into contact with the non-functional monomer, or after the modification target on which non-functional polymer chains are formed is brought into contact with the fluoropolyether segment-containing functional monomer, a reducing agent or antioxidant may further be added thereto. Alternatively, these components may be mixed together in advance before the material mixture is brought into contact with the modification target or the modification target on which non-functional polymer chains are formed.

Specifically, non-functional polymer chains and functional polymer chains may be sequentially formed by radical polymerization of the respective monomers as follows. For example, a step is performed in which light is irradiated after the modification target obtained in the step 1, on the surface of which polymerization initiation points are formed from the photopolymerization initiator, is brought into contact (e.g., immersion, application) with the (liquid) non-functional monomer or a solution thereof, which contains a solution of a reducing agent or antioxidant added, or after the modification target is brought into contact with the (liquid) non-functional monomer or a solution thereof and then a solution of a reducing agent or antioxidant is put thereon. Then, the modification target on which non-functional polymer chains are formed is subjected to a similar step using the (liquid) fluoropolyether segment-containing functional monomer or a solution thereof, and a solution of a reducing agent or antioxidant.

For example, in the case of using a fluoropolyether segment-containing functional monomer that has a specific gravity of more than 1 and is not miscible with water, a solution of a reducing agent or antioxidant is located over the (liquid) radically polymerizable monomer or a solution thereof while being separated therefrom.

The reducing agent or antioxidant is not particularly limited and may be any appropriate compound that functions as such an agent. Examples include vitamins A such as retinol, dehydroretinol, retinol acetate, retinol palmitate, retinal, retinoic acid, and vitamin A oil, and derivatives or salts thereof; carotenoids such as α-carotene, β-carotene, γ-carotene, cryptoxanthin, astaxanthin, and fucoxanthin, and derivatives thereof; vitamins B such as pyridoxine, pyridoxal, pyridoxal-5-phosphate, and pyridoxamine, and derivatives or salts thereof; vitamins C such as ascorbic acid, sodium ascorbate, ascorbyl stearate, ascorbyl palmitate, ascorbyl dipalmitate, and magnesium ascorbyl phosphate, and derivatives or salts thereof; vitamins D such as ergocalciferol, cholecalciferol, and 1,2,5-dihydroxy-cholecalciferol, and derivatives or salts thereof; vitamins E such as α-tocopherol, β-tocopherol, γ-tocopherol, δ-tocopherol, α-tocotrienol, β-tocotrienol, γ-tocotrienol, δ-tocotrienol, tocopherol acetate, and tocopherol nicotinate, and derivatives or salts thereof; trolox and derivatives or salts thereof; dihydroxytoluene, butylhydroxytoluene, butylhydroxyanisole, dibutylhydroxytoluene, α-lipoic acid, dehydrolipoic acid, and glutathione, and derivatives or salts thereof; uric acid, erythorbic acid, and erythorbates such as sodium erythorbate, and derivatives or salts thereof; gallic acid and gallates such as propyl gallate, and derivatives or salts thereof; rutin and rutins such as α-glycosylrutin, and derivatives or salts thereof; tryptophan and derivatives or salts thereof; histidine and derivatives or salts thereof; cysteine derivatives or salts such as N-acetylcysteine, N-acetylhomocysteine, N-octanoylcysteine, and N-acetylcysteine methyl ester; cystine derivatives or salts such as N,N'-diacetylcystine dimethyl ester, N,N'-dioctanoylcystine dimethyl ester, and N,N'-dioctanoylhomocystine dimethyl ester; carnosine and derivatives or salts thereof; homocarnosine and derivatives or salts thereof; anserine and derivatives or salts thereof; carcinine and derivatives or salts thereof; dipeptide or tripeptide derivatives or salts containing histidine and/or tryptophan and/or histamine; flavonoids such as flavanone, flavone, anthocyanin, anthocyanidin, flavonol, quercetin, quercitrin, myricetin, fisetin, hamamelitannin, catechin, epicatechin, gallocatechin, epigallocatechin, epicatechin gallate, and epigallocatechin gallate; tannic acid, caffeic acid, ferulic acid, protocatechuic acid, calcone, oryzanol, carnosol, sesamol, sesamine, sesamolin, zingerone, curcumin, tetrahydrocurcumin, clovamide, deoxyclovamide, shogaol, capsaicine, vanillylamide, ellagic acid, bromphenol, flavoglaucin, melanoidin, riboflavin, riboflavin butyrate, flavin mononucleotide, flavin adenine nucleotide, ubiquinone, ubiquinol, mannitol, bilirubin, cholesterol, ebselen, selenomethionine, ceruloplasmin, transferrin, lactoferrin, albumin, superoxide dismutase, catalase, glutathione peroxidase, metallothionein, and O-phosphono-pyridoxylidene rhodamine. These compounds may be used alone or in combination of two or more.

Among these, riboflavin, ascorbic acid, α-tocopherol, β-carotene, and uric acid are preferred, and riboflavin and ascorbic acid are particularly preferred, because of their high oxygen-scavenging capability.

In the case of using a solution of a reducing agent or antioxidant, the concentration of the reducing agent or antioxidant is preferably $10^{-4}$ to 1% by mass, more preferably $10^{-3}$ to 0.1% by mass.

Moreover, the amounts of the radically polymerizable monomers may be appropriately set depending on, for example, the length of polymer chain to be formed, or the properties to be provided by the chains. Also, the amount of the reducing agent or antioxidant may be appropriately set in view of the capability of scavenging oxygen in the system, or the like.

The solvent for application (spraying), the method for application (spraying), the method for immersion, the conditions for irradiation, and the like may be conventionally known materials or methods. The solutions of the radically polymerizable monomers may each be an aqueous solution, or a solution in an organic solvent that does not dissolve the photopolymerization initiator used, e.g., benzophenone compound. Furthermore, the (liquid) radically polymerizable monomers, or a solution thereof may contain a known polymerization inhibitor such as 4-methylphenol.

In the present invention, the radical polymerization of the non-functional monomer or the fluoropolyether segment-containing functional monomer is allowed to proceed by light irradiation after the application of the (liquid) monomer or a solution thereof or after the immersion in the monomer or a solution thereof. Here, UV light sources with an emission wavelength mainly in the ultraviolet region, such as high-pressure mercury lamps, metal halide lamps, and LED lamps, can be suitably used. The light dose may be appropriately set in view of polymerization time and uniformity of the reaction. Moreover, in order to prevent inhibition of polymerization due to active gas such as oxygen in the reaction container, oxygen is preferably removed from the reaction container and the reaction solution during or before the light irradiation. Thus, for example, a method may appropriately be employed in which an inert gas, such as nitrogen gas or argon gas, is inserted into the reaction container and the reaction solution to discharge active gas such as oxygen from the reaction system and thereby replace the atmosphere in the reaction system with the inert gas. Also, in order to prevent inhibition of the reaction due to oxygen or the like, for example, a measure may appropriately be taken in which a UV light source is disposed so that no air layer (oxygen content: 15% or higher) exists between the reaction container made of glass, plastics or the like and the reaction solution or the modification target.

In the case of irradiation with ultraviolet light, the ultraviolet light preferably has a wavelength of 300 to 450 nm, more preferably 300 to 400 nm. Such light allows polymer chains to be formed well on the surface of the modification target. The light source may be a high-pressure mercury lamp, an LED with a center wavelength of 365 nm, an LED with a center wavelength of 375 nm, or the like. In particular, preferred is irradiation with LED light having a wavelength of 300 to 400 nm, more preferably LED light having a wavelength of 355 to 380 nm. LEDs or the like which have a center wavelength of 365 nm, which is close to the excitation wavelength 366 nm of benzophenone, are particularly preferred in view of efficiency.

Moreover, the polymer chains including functional polymer chains formed in the step 2 provide excellent sliding properties and excellent durability while maintaining good sealing properties. The formed polymer chains preferably each have a polymerization degree of 20 to 200000, more preferably 350 to 50000.

The length of the entire polymer chain, including the non-functional polymer chain and the functional polymer chain, formed in the step 2, is preferably 10 to 50000 nm, more preferably 100 to 50000 nm. If the length is shorter than 10 nm, good sliding properties tend not to be achieved. If the length is longer than 50000 nm, a further improvement in sliding properties cannot be expected while the cost of raw materials tends to increase due to the use of the expensive monomer. In addition, surface patterns generated by the surface treatment tend to be visible to the naked eyes and thereby spoil the appearance and decrease sealing properties.

Regarding the entire polymer chain formed in the step 2, the ratio in length of the non-functional polymer chain to the functional polymer chain [(length of non-functional polymer chain):(length of functional polymer chain)] is preferably 50:50 to 99.9:0.1, more preferably 90:10 to 99.5:0.5. If the length of the functional polymer chain is shorter than 0.1%, desired functions may not be provided, while if it exceeds 50%, there tends to be an economic disadvantage.

In the step 2, two or more types of non-functional monomers may simultaneously be radically polymerized starting from the polymerization initiation points, and two or more types of fluoropolyether segment-containing functional monomers may simultaneously be radically polymerized. Moreover, two or more layers of non-functional or functional polymer chains may be stacked. Furthermore, multiple types of polymer chains may be grown on the surface of the modification target. In the surface modification method of the present invention, the polymer chains may be cross-linked to one another. In this case, the polymer chains may be cross-linked to one another by ionic cross-linking, crosslinking by a hydrophilic group containing an oxygen atom, or crosslinking by a halogen group such as iodine.

The surface modification method may be applied to a rubber vulcanizate or a thermoplastic elastomer to prepare a surface-modified elastic body. For example, surface-modified elastic bodies that are excellent in sliding properties in the presence of water or in a dry state can be prepared. Such surface-modified elastic bodies are also excellent in that they have low friction and low water resistance or drag. Moreover, the method may be applied to at least a part of a three-dimensional solid (e.g. elastic body) to prepare a surface-modified elastic body with modified properties. Furthermore, preferred examples of such surface-modified elastic bodies include polymer brushes. The polymer brush as used herein means an assembly of graft polymer molecules obtained in the "grafting from" approach by surface-initiated living radical polymerization. The graft chains are preferably oriented in a direction substantially vertical to the surface of the modification target because then entropy is reduced and thus the molecular mobility of the graft chains is reduced to provide sliding properties. Moreover, semidilute or concentrated brushes which have a brush density of 0.01 chains/nm$^2$ or higher are preferred.

Furthermore, the surface modification method may be applied to a rubber vulcanizate or a thermoplastic elastomer to prepare a gasket for syringes at least part of whose surface is modified. Preferably, at least the sliding portion of the surface of the gasket is modified. The entire surface of the gasket may be modified.

FIG. 1 is an exemplary side view of an embodiment of a gasket for syringes. A gasket 1 shown in FIG. 1 has three circular protruding portions 11a, 11b and 11c which continuously protrude along the circumferential direction on the outer periphery that is to be in contact with the inner periphery of a syringe barrel. Examples of portions of the gasket 1 to which the surface modification can be applied include: (1) the surfaces of protruding portions to be in contact with a syringe barrel, such as the circular protruding portions 11a, 11b and 11c; (2) the entire side surface including the circular protruding portions 11a, 11b and 11c; and (3) both the entire side surface and a bottom surface 13.

Furthermore, if the surface modification method is applied to the grooves formed on the tread of tires for use on vehicles such as passenger cars to create a polymer brush on the grooves, the fluid resistance of the groove surface on wet or snowy roads is reduced, and the contact angle with water is increased. Thus, the abilities to remove and drain water or snow can be enhanced, resulting in improved grip performance.

Figure 2:
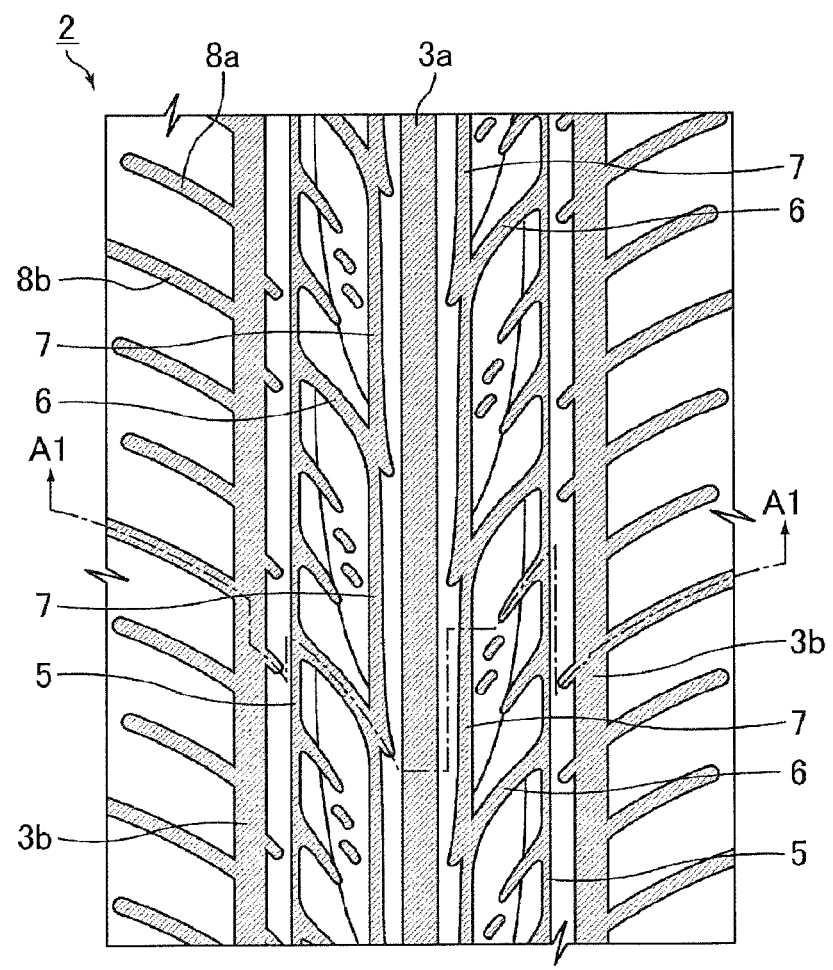
FIG. 2 is an exemplary development view of a tread portion of a pneumatic tire (the whole tire is not shown).
Figure 3:
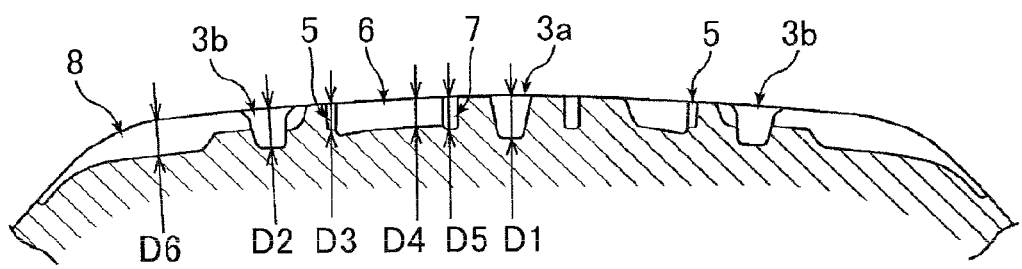
FIG. 3 is an exemplary A1-A1 cross-sectional view of FIG. 2.

FIG. 2 is an exemplary development view of a tread portion 2 of a pneumatic tire (the whole tire is not shown). FIG. 3 is an exemplary A1-A1 cross-sectional view of FIG. 2.

In FIGS. 2 and 3, a longitudinal center groove 3a (groove depth D1) and longitudinal shoulder grooves 3b (groove depth D2) are straight grooves linearly extending in the circumferential direction of the tire. Such straight grooves can contribute to low drainage resistance and high drainage performance during straight travelling.

The pneumatic tire also has fine grooves 5 (groove depth D3) extending in the tire circumferential direction on the side of the longitudinal shoulder groove 3b; beveled intermediate grooves 6 (groove depth D4) extending with an inclination from the fine groove 5 toward the longitudinal center groove 3a; connecting grooves 7 (groove depth D5) located inward of the fine groove 5 in the axis direction of the tire and connecting the beveled intermediate grooves 6 next to one another in the circumferential direction of the tire; lateral shoulder grooves 8, 8a and 8b (groove depth D6) extending from the longitudinal shoulder groove 3b toward the outside of the tire; and the like. These grooves can also contribute to drainage performance. If the method is applied to these grooves, the above-mentioned effects can be achieved.

EXAMPLES

The following will describe the present invention in more detail referring to non-limiting examples.

Example 1

A chlorobutyl rubber (degree of unsaturation: 1 to 2%) containing isoprene units was cross-linked by triazine to prepare a vulcanized rubber gasket (vulcanized at 180° C. for 10 minutes), which was then immersed in a 3 wt % acetone solution of benzophenone so that benzophenone was adsorbed onto the surface of the rubber vulcanizate, followed by drying. Then the surface of the vulcanized rubber gasket was irradiated with LED-UV light having a wavelength of 365 nm for 30 minutes to chemically bond benzophenone to the surface. Thereafter, the surface was washed with acetone to remove unreacted benzophenone. The resulting rubber vulcanizate was taken out and dried.

The dried vulcanized rubber gasket was immersed in an aqueous acrylic acid solution (2.5 M, 18 g of acrylic acid dissolved in 100 mL of water) in a glass reaction container. Then the gasket was irradiated with LED-UV light having a wavelength of 365 nm for 30 minutes to cause radical polymerization and grow non-functional polymer chains (polyacrylic chains) on the surface of the rubber. Then, the surface was washed with water and dried.

Next, a 20% by mass solution of a fluoropolyether segment-containing functional monomer (DAC-HP produced by Daikin Industries, Ltd.) was applied to the surface of the vulcanized rubber gasket where polyacrylic acid was grown. Then the surface was irradiated with LED-UV light having a wavelength of 365 nm for 10 minutes in an argon gas atmosphere to cause radical polymerization and further grow fluoropolyether segment-containing functional polymer chains on the polyacrylic acid chains (non-functional polymer chains). In this manner, a surface-modified elastic body (a polymer brush layer on the surface) was obtained.

Example 2

A surface-modified elastic body was obtained as in Example 1, except that the polymerization time of the functional monomer was changed to 15 minutes.

Comparative Example 1

A chlorobutyl rubber (degree of unsaturation: 1 to 2%) containing isoprene units was cross-linked by triazine to prepare a rubber vulcanizate (vulcanized at 180° C. for 10 minutes), which was then used as it was.

Comparative Example 2

A surface-modified elastic body was obtained as in Example 1, except that only the fluoropolyether segment-containing functional polymer chains were grown without forming the non-functional polymer chains on the surface of the vulcanized rubber gasket.

The surface-modified elastic bodies prepared in the examples and comparative examples were evaluated by the methods mentioned below.

(Length of Polymer Chain)

To determine the length of the polymer chain formed on the surface of the rubber vulcanizate, a cross section of the modified rubber having polymer chains formed thereon was measured with an SEM at an accelerating voltage of 15 kV and a magnification of 1000 times. The thickness of the polymer layer photographed was determined and used as the length of the polymer chain.

(Friction Resistance)

To determine the friction resistance of the surface of the surface-modified elastic body, the vulcanized rubber gaskets prepared in the examples and comparative examples were each inserted into a COP resin barrel of a syringe and then pushed towards the end of the barrel (push rate: 30 mm/min) using a tensile tester while friction resistance was measured. The values of the examples are expressed as a friction resistance index using the equation below, with the friction resistance of Comparative Example 1 being set equal to 100. A lower index indicates a lower friction resistance.

(Friction resistance index)=(Friction resistance of each example)/(Friction resistance of Comparative Example 1)×100

TABLE 1

|  | Example | | Comparative Example | |
| --- | --- | --- | --- | --- |
|  | 1 | 2 | 1 | 2 |
| Length of entire polymer chain (nm) | 11500 | 12000 | — | 1800 |
| [Non-functional polymer chain]:[Functional polymer chain] (in length) | 98:2 | 97:3 | — | — |
| Friction resistance index | 1.25 | 1.63 | 100 | 60 |

The results of Table 1 demonstrate that the surfaces of the surface-modified elastic bodies of the examples exhibited greatly reduced friction resistances and therefore had good sliding properties. In addition, since only the surface was modified, the sealing properties of these surface-modified elastic bodies were similar to Comparative Example 1.

Thus, when these surface-modified elastic bodies are used as gaskets for syringe plungers, they provide sufficient sealing properties while reducing the friction of the plunger with the syringe barrel, and therefore they enable easy and accurate treatment with syringes. Moreover, since they have a small difference between static and kinetic friction coefficients, the start of pushing the plunger and the subsequent inward movement of the plunger can be smoothly carried out without pulsation. Also, if polymer chains are formed on the inner surface of a syringe barrel made of a thermoplastic elastomer, treatment with the syringe can be readily carried out, similarly as described above.

Furthermore, the above-mentioned effects can also be expected when polymer chains are formed on the surfaces of the grooves formed on the tread or of the sidewalls of tires for use on vehicles such as passenger cars, on the surfaces of diaphragms, on the sliding surfaces of skis or snowboards, or on the surfaces of swimsuits, road signs, sign boards, or the like.

REFERENCE SIGNS LIST

1: Gasket
11a, 11b, 11c: Circular protruding portion
13: Bottom surface
2: Tread portion
3a: Longitudinal center groove
3b: Longitudinal shoulder groove
5: Fine groove
6: Beveled intermediate groove
7: Connecting groove
8, 8a, 8b: Lateral shoulder groove

The invention claimed is:

1. A method for surface-modifying a rubber vulcanizate or a thermoplastic elastomer as a target for modification, the method comprising:
   step 1 of forming polymerization initiation points on a surface of the rubber vulcanizate or the thermoplastic elastomer; and
   step 2 of radically polymerizing a non-functional monomer, starting from the polymerization initiation points, to form non-functional polymer chains, and then radically polymerizing a fluoropolyether segment-containing functional monomer on the resultant non-functional polymer chains to form functional polymer chains while extending the polymer chains;
   wherein the non-functional monomer is at least one member selected from acrylic acid, acrylic acid esters, acrylamide, dimethylacrylamide, diethylacrylamide, isopropylacrylamide, hydroxyacrylamide, acryloylmorpholine, acrylic acid alkali metal salts, acrylic acid amine salts, methacrylic acid, methacrylic acid esters, methacrylamide, methacrylic acid alkali metal salts, methacrylic acid amine salts, and acrylonitrile.

2. The method according to claim 1,
   wherein the step 1 comprises adsorbing a photopolymerization initiator onto a surface of the modification target, optionally followed by irradiation with LED light having a wavelength of 300 to 400 nm, to form polymerization initiation points from the photopolymerization initiator on the surface.

3. The method according to claim 1,
   wherein the step 2 comprises radically polymerizing a non-functional monomer, starting from the polymerization initiation points, by irradiation with LED light having a wavelength of 300 to 450 nm to grow non-functional polymer chains, and then radically polymerizing a fluoropolyether segment-containing functional monomer by irradiation with LED light having a wavelength of 300 to 450 nm to grow functional polymer chains.

4. The method according to claim 1,
wherein the rubber vulcanizate or thermoplastic elastomer contains an allylic carbon atom which is adjacent to a double bond.

5. The method according to claim 2,
wherein the photopolymerization initiator is at least one of a benzophenone compound and a thioxanthone compound.

6. The method according to claim 1,
wherein in the step 2, a reducing agent or an antioxidant is added in the radical polymerization of the non-functional monomer and/or of the fluoropolyether segment-containing functional monomer.

7. The method according to claim 6,
wherein the reducing agent or antioxidant is at least one selected from the group consisting of riboflavin, ascorbic acid, α-tocopherol, β-carotene, and uric acid.

8. The method according to claim 2,
wherein the method comprises inserting an inert gas into a reaction container and a reaction solution during or before the light irradiation, and polymerizing the monomer in an atmosphere replaced with the inert gas.

9. The method according to claim 1,
wherein the fluoropolyether segment in the fluoropolyether segment-containing functional monomer is a perfluoropolyether segment comprising at least one of the following units (A) to (D):
(A): —$(CF_2O)_a$—,
(B): —$(CF_2CF_2O)_b$—,
(C): —$(CF_2CF_2CF_2O)_c$—, and
(D): —$(CF(CF_3)CF_2O)_d$—
wherein a, b, c, and d each represent 0 or a positive integer and satisfy the relation: $2 \leq a+b+c+d \leq 200$.

10. The method according to claim 1,
wherein the fluoropolyether segment-containing functional monomer is a monomer represented by the following formula:

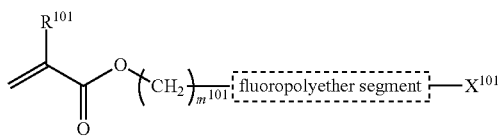

wherein $R^{101}$ represents a methyl group, an ethyl group, a hydrogen atom, a fluorine atom, a chlorine atom, or a bromine atom; $m^{101}$ represents an integer of 0 to 5; $X^{101}$ represents a hydrogen atom or a fluorine atom; and the fluoropolyether segment is a perfluoropolyether segment comprising at least one of the following units (A) to (D):
(A): —$(CF_2O)_a$—,
(B): —$(CF_2CF_2O)_b$—,
(C): —$(CF_2CF_2CF_2O)_c$—, and
(D): —$(CF(CF_3)CF_2O)_d$—
wherein a, b, c, and d each represent 0 or a positive integer and satisfy the relation: $2 \leq a+b+c+d \leq 200$.

11. The method according to claim 1,
wherein the fluoropolyether segment-containing functional monomer is a monomer represented by the following formula:

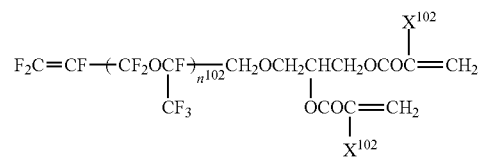

wherein $n^{102}$ represents an integer of 0 to 100; and $X^{102}$ represents H or F.

12. The method according to claim 1,
wherein the (liquid) monomer or a solution thereof contains a polymerization inhibitor, and is polymerized in the presence of the polymerization inhibitor.

13. The method according to claim 12,
wherein the polymerization inhibitor is 4-methylphenol.

14. The method according to claim 1,
wherein a length of the entire polymer chain, including the non-functional polymer chain and the functional polymer chain, is 10 to 50000 nm.

15. The method according to claim 1,
wherein a ratio in length of the non-functional polymer chain to the functional polymer chain is 50:50 to 99.9:0.1.

16. A surface-modified elastic body, which is obtained by the method according to claim 1.

17. A surface-modified elastic body, which is obtained by the method according to claim 1, the elastic body having sliding properties, low friction, or low water resistance in the presence of water or in a dry state.

18. A surface-modified elastic body, comprising a three-dimensional solid at least part of whose surface is modified by the method according to claim 1.

19. The surface-modified elastic body according to claim 16, which comprises a polymer brush.

20. A gasket for syringes, at least part of whose surface is modified by the method according to claim 1.

21. A tire, at least part of whose groove surface is modified by the method according to claim 1.

* * * * *